United States Patent
Hodge et al.

(10) Patent No.: US 11,931,236 B2
(45) Date of Patent: Mar. 19, 2024

(54) VAGINAL DILATOR ASSEMBLIES

(71) Applicant: MEDSTAR HEALTH, INC., Columbia, MD (US)

(72) Inventors: Andrew Hodge, Baltimore, MD (US); Colleen Lindo, Baltimore, MD (US); Gabriel Del Corral, Baltimore, MD (US); Angela Jaimes, Baltimore, MD (US)

(73) Assignee: MEDSTAR HEALTH, INC., Columbia, MD (US)

( * ) Notice: Subject to any disclaimer, the term of this patent is extended or adjusted under 35 U.S.C. 154(b) by 153 days.

(21) Appl. No.: 17/211,918

(22) Filed: Mar. 25, 2021

(65) Prior Publication Data

US 2022/0304792 A1 Sep. 29, 2022

(51) Int. Cl.
*A61F 2/04* (2013.01)
*A61F 2/00* (2006.01)

(52) U.S. Cl.
CPC .............. *A61F 2/0059* (2013.01); *A61F 2/04* (2013.01); *A61F 2220/0075* (2013.01); *A61F 2250/0039* (2013.01); *A61M 2210/1475* (2013.01)

(58) Field of Classification Search
CPC .. A61F 2/0059; A61F 2/04; A61F 2220/0075; A61F 2250/0039; A61M 2210/1475
See application file for complete search history.

(56) References Cited

U.S. PATENT DOCUMENTS

| | | | | |
|---|---|---|---|---|
| 5,681,340 | A * | 10/1997 | Veronikis | A61M 29/00 600/207 |
| 6,575,987 | B2 * | 6/2003 | Gellman | A61B 17/00234 606/232 |
| 6,623,503 | B1 * | 9/2003 | Thomas | A61M 29/00 606/191 |
| 10,166,087 | B2 * | 1/2019 | Aravena | A61C 1/082 |
| 10,548,634 | B2 * | 2/2020 | Gemmer | A61M 29/00 |
| 10,722,358 | B2 * | 7/2020 | Pintor | A61F 2/2412 |
| 2007/0043388 | A1 * | 2/2007 | Greenwood | A61M 29/00 606/193 |
| 2008/0234719 | A1 * | 9/2008 | Adams | A61M 29/00 606/191 |
| 2013/0296643 | A1 * | 11/2013 | Hoyte | A61F 2/0045 600/37 |
| 2016/0235492 | A1 * | 8/2016 | Morard | A61B 17/1757 |

(Continued)

FOREIGN PATENT DOCUMENTS

WO WO-2019036776 A1 * 2/2019 ............. A61B 17/42

*Primary Examiner* — Suzette J Gherbi
(74) *Attorney, Agent, or Firm* — TAROLLI, SUNDHEIM, COVELL & TUMMINO L.L.P.

(57) ABSTRACT

Vaginal dilator assemblies, devices and kits. Assemblies can include a base, and an adapter. The base can have an inner portion and the adapter can have an outer portion that is complimentary to the inner portion of the base such that the adapter is non-rotatably fitted into the base. Vaginal dilator devices can include a base defining a recess aligned with the longitudinal axis of the base. The recess can have a plurality of step tapered sections. Vaginal dilator kits are also provided that include a plurality of vaginal dilators having different diameters. Each of the plurality of vaginal dilators is configured to be axially aligned and securely fitted into one of the step tapered sections of the recess of the base.

12 Claims, 5 Drawing Sheets

(56) References Cited

U.S. PATENT DOCUMENTS

| | | | |
|---|---|---|---|
| 2016/0287063 A1* | 10/2016 | Ramanujam | A61B 1/00087 |
| 2021/0137626 A1* | 5/2021 | Scholten | A61B 46/10 |
| 2022/0105242 A1* | 4/2022 | Carter | A61B 17/86 |
| 2022/0249179 A1* | 8/2022 | Morard | A61B 17/1757 |
| 2022/0280282 A1* | 9/2022 | Khouri | A61B 17/06066 |

* cited by examiner

VAGINAL DILATOR ASSEMBLIES

TECHNICAL FIELD

The present application relates to vaginal dilator assemblies for penile inversion vaginoplasty surgery.

BACKGROUND

A vaginoplasty is a surgical procedure where a vagina is created in a patient. Such a procedure involves removing the patient's penis, as well as the testicles and scrotum, if an orchiectomy was not previously performed. A vaginoplasty involves rearranging the patient's current tissue in the genital area to create a vaginal canal, external genitalia, and the labia. To create the vaginal canal, the surgeon uses the skin surrounding the existing penis and/or scrotum. An additional skin graft from the abdomen or thigh may be used to achieve a full vaginal canal. In particular, a vaginoplasty technique is some variation of the penile inversion procedure. In a one-stage vaginoplasty, a vaginal vault is created between the patient's rectum and the urethra, in the same location as a non-transgender female between the pelvic floor muscles. The vaginal lining is created from penile skin or scrotal skin. In order to create the vaginal vault, the penile/scrotal skin is stretched over a silicone vaginal dilator, the hair from the skin is removed and thinned, and the skin is sutured into a pocket to create the labia majora and the clitoris.

Current vaginal dilators are not designed for this purpose and do not stand upright for correct positioning during formation of the vaginal graft. Accordingly, there is a need for a vaginal dilator holder or stand that allows the vaginal dilator to maintain the correct position during vaginal graft formation.

SUMMARY

The present disclosure relates to vaginal dilator assemblies, devices, and kits. Assemblies can include a base comprising a base body having an inner portion and defining a recess aligned with the longitudinal axis of the base. Assemblies can also include an adapter comprising an adapter body defining an opening through a top portion thereof. The adapter body can be axially aligned with the recess of the base body and have an outer portion complimentary to the inner portion of the base body such that the adapter body is non-rotatably fitted into the recess of the base body.

A vaginal dilator device can include a base comprising a base body having an inner wall defining a recess aligned with the longitudinal axis of the base. The recess can have a plurality of step tapered sections sized and configured to receive vaginal dilators having different diameters.

DETAILED DESCRIPTION

Figure 1:
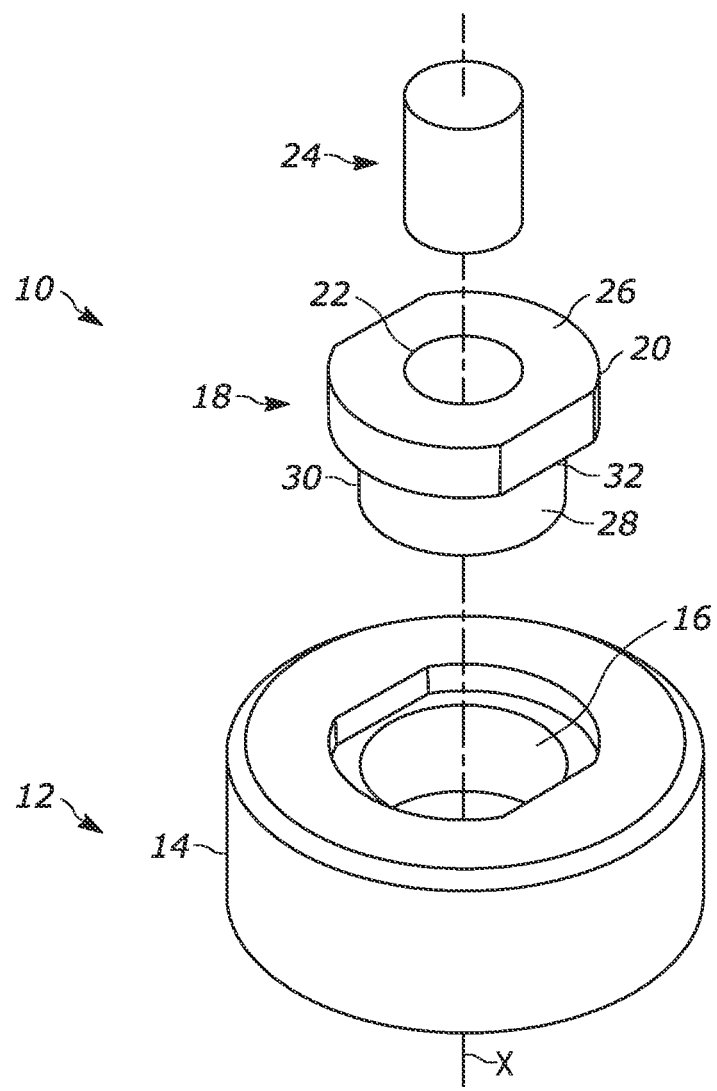
FIG. 1 is an exploded view of a vaginal dilator assembly according to an exemplary aspect of the present disclosure.

The present disclosure relates to vaginal dilator assemblies and kits. In particular, the present disclosure provides a support structure to hold various sizes of vaginal dilators in an upright position. In the present context, a vaginal dilator is a device that is shaped and configured to maintain the vaginal pocket after a vaginoplasty procedure and/or a device shaped and configured to create the vaginal pocket during a vaginoplasty procedure. As used herein with respect to a described element, the terms "a," "an," and "the" include at least one or more of the described element(s) including combinations thereof unless otherwise indicated. Further, the terms "or" and "and" refer to "and/or" and combinations thereof unless otherwise indicated. By "substantially" is meant that the shape or configuration of the described element need not have the mathematically exact described shape or configuration of the described element but can have a shape or configuration that is recognizable by one skilled in the art as generally or approximately having the described shape or configuration of the described element. As such "substantially" refers to the complete or nearly complete extent of a characteristic, property, state, or structure. The exact allowable degree of deviation from the characteristic, property, state, or structure will be so as to have the same overall result as if the absolute characteristic, property, state, or structure were obtained. The terms "left," "right," "top" and "bottom" refer to the position of elements as they are depicted in the drawings and the terms "left" and "right" can be interchanged unless indicated otherwise. The terms "first," "second," etc. are used to distinguish one element from another and not used in a quantitative sense unless indicated otherwise. Thus, a "first" element described below could also be termed a "second" element. By "integral" or "integrated" is meant that the described components are fabricated as one piece or multiple pieces affixed during manufacturing such that the components are a unitary and continuous piece after manufacturing. Such described components are not separable without damaging the integrity (i.e. tearing) of either of the components as opposed to two-piece or multi-piece components that are assembled together after manufacturing, such as prior to or during surgical insertion, and where the components can be separated. As used herein a "patient" includes a mammal such as a human being. All device, assemblies, and kits as described herein are used for medical purposes and are therefore sterile. Vaginal dilator assemblies and kits as disclosed herein can be used with vaginal dilators as disclosed herein as well as other vaginal dilators. Although the drawings show certain elements of a vaginal dilator assembly or kit in combination, it should be noted that such elements can be included in other embodiments or aspects illustrated in other drawings or otherwise described in the specification. In other words, each of the disclosed aspects and embodiments of the present disclosure may be considered individually or in combination with other aspects and embodiments of the disclosure including patent applications incorporated by reference herein.

As stated above, during construction of a vaginal graft in a vaginoplasty procedure or after a vaginoplasty procedure, a vaginal dilator should be positioned upright. Some form of a stand is needed to hold the vaginal dilator. Current stands are either too large such that the dilator rotates uncontrollably or the dilator is otherwise unstable on the stand. Vaginal dilator assemblies as disclosed herein include a stable base that holds a vaginal dilator in an upright position to stabilize the vaginal dilator during the construction of a vaginal graft during penile inversion vaginoplasty surgery or after such a procedure. In particular, in certain aspects, vaginal dilator assemblies include at least two parts: a base and an adapter. Vaginal dilators of various diameters can fit inside a correctly sized adapter, which nests inside the base. The base and adapter are configured such that the adapter does not rotate in the base. The base and adapter can have complimentary features to achieve such functionality.

In an aspect, a vaginal dilator assembly comprises a base comprising a base body having an inner portion and defining a recess that is aligned with the longitudinal axis of the base. The base can be fabricated from a stable material such as, for example, aluminum or stainless steel. The assembly can further include an adapter comprising an adapter body defining an opening through a top portion thereof. The adapter body is axially aligned with the recess of the base body and has an outer portion complimentary to the inner portion of the base body such that the adapter body is non-rotatably fitted in the recess of the base body. The assembly can include adapters of various different sizes. The vaginal dilator assembly can further include a vaginal dilator axially aligned with and received by the opening of the adapter body.

Figure 2:
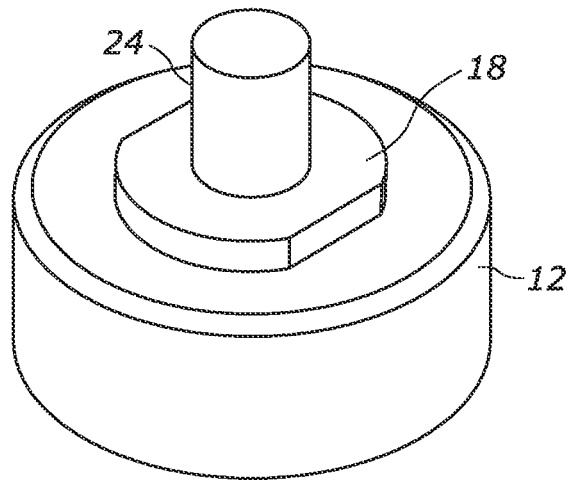
FIG. 2 is a perspective view of the vaginal dilator assembly of FIG. 1 in an assembled configuration.
Figure 3:
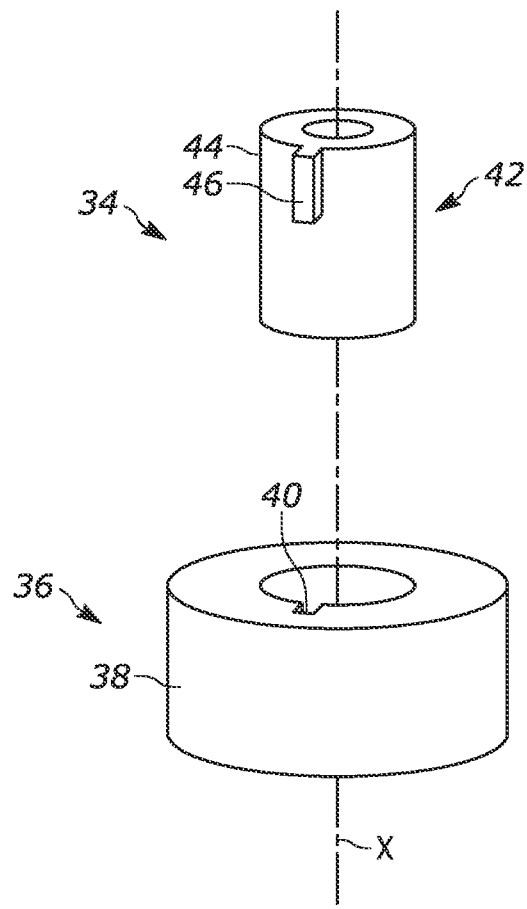
FIG. 3 is an exploded view of a vaginal dilator assembly according to an exemplary aspect of the present disclosure.
Figure 4:
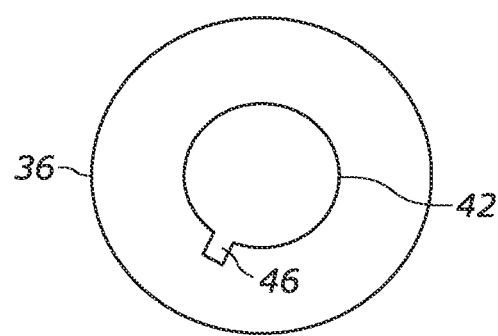
FIG. 4 is a top view of the vaginal dilator assembly of FIG. 3 in an assembled configuration.

The inner portion of the base body and the complimentary outer portion of the adapter body can have various different configurations so long as the adapter is non-rotatably fitted into the base. For example, with reference to FIGS. 1 and 2, a vaginal dilator assembly 10 can comprise a base 12 having a base body 14 where the inner portion defines the recess, which is aligned with longitudinal axis X of base 12. In this illustrated aspect, the recess is a stepped recess 16 although the recess could have other configurations. Adapter 18 of assembly 10 has an adapter body 20 defining an opening 22 through a top portion 26 thereof. Adapter body 20 is axially aligned with recess 16 of base body 14. In this illustrated aspect, adapter 20 has a head 26 and a shank 28 and the outer portion of the adapter that is complimentary to the inner portion of the base is the outer surface 30 of shank 28 and optionally at least part of the lower surface 32 of head 26 (and optionally part of the side surfaces of the head). Referring to FIGS. 3 and 4, in another aspect, a vaginal dilator assembly 34 includes a base 36 comprising a base body 38 where the inner portion defines a channel 40 that extends at least partially along the longitudinal axis X of base 36. Adapter 42 comprises an adapter body 44 where the outer portion comprises a notch or other projection 46 that is complimentary to channel 40 of base body 38.

As mentioned above, the adapter can have different sizes. For example, the opening in the adaptor can come in various sizes to fit various diameters of dilator. Additionally or alternatively, the adapter could be configured with various fitting mechanism such as a balloon or wedge, that can be inflated/inserted to decrease the space between the adaptor (or base itself) and the dilator. The adaptors serve to fit different dilator diameters. If the base itself has a balloon or can accept a wedge, the adaptors are not necessarily needed. However, the adaptors can be shaped and configured for a specific dilator product so the adaptors may not necessarily need to perfectly fit a different dilator product and could benefit from a fitting mechanism.

Referring back to FIG. 1, vaginal dilator assembly 10 can further include a vaginal dilator 24 axially aligned with and received by opening 22 of adapter 18. A similar vaginal dilator can be used with the vaginal dilator assembly illustrated in FIGS. 3 and 4.

All components of the assembly can be separate, individual components or different components can be combined into an integral, one-piece device. For example, the adapter and dilator can be integrated into a single device to fit into the base or the dilator, adapter and base can be integrated into one continuous device.

Figure 5:
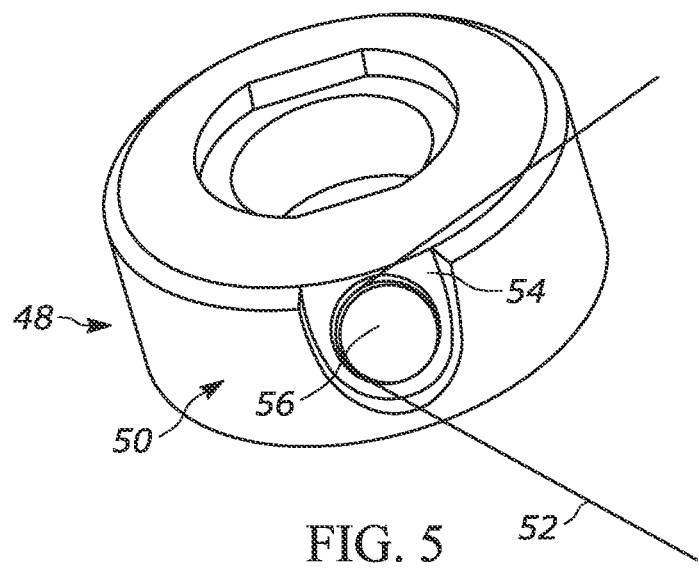
FIG. 5 is a perspective view of a base of a vaginal dilator assembly according to an exemplary aspect of the present disclosure.
Figure 6:
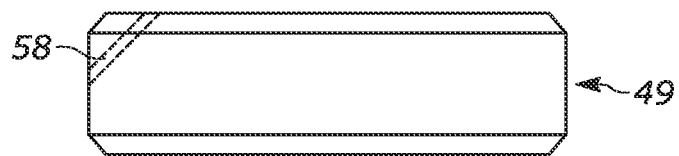
FIG. 6 is a side view of a base of a vaginal dilator assembly according to an exemplary aspect of the present disclosure.
Figure 7:
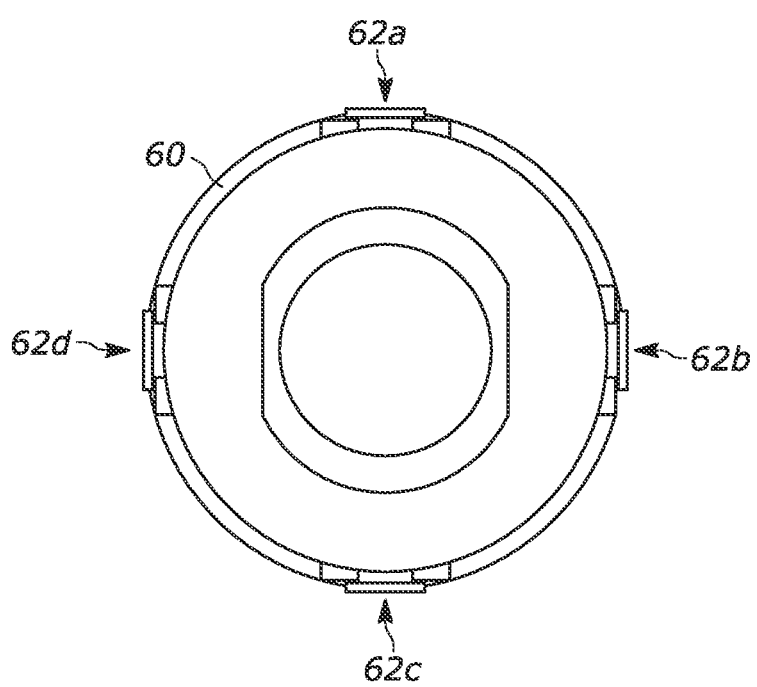
FIG. 7 is top view of a base of a vaginal dilator assembly according to exemplary aspect of the present disclosure.

Referring to FIGS. 5-7, the base 48 of a vaginal dilator assembly can comprise a plurality of securers circumferentially disposed about the base body 50 and configured to receive and secure elastic stays 52 or sutures to base 48. Such elastic stays can be threaded through/onto the securers such that the skin tissue placed on the vaginal dilator can be pulled down as it is being sutured into the appropriately shaped pocket. The securers can comprise any structure that can secure elastic stays to base 48. FIG. 5 illustrates the securer as a groove 54 and post 56 and FIG. 6 illustrates a base 49 where the securer is a channel 58. The securers can have other configuration so long as they perform the function of securing elastic stays or other retractors to the base. For example, the securers could be V-shaped channels, boat-style cleats, wedge-shaped flaps, or other types of projections. FIGS. 5 and 6 only illustrate one securer for the purposes of clarity, but the base can comprise a plurality of securers to allow for multiple stays, such as three or four, to pull skin tissue downward on the vaginal dilator. For example, referring to FIG. 7, a base 60 can comprise a plurality of securers 62, such as four securers equidistantly spaced from each other (e.g. at the 12:00; 3:00; 6:00 and 9:00 position).

Figure 8:
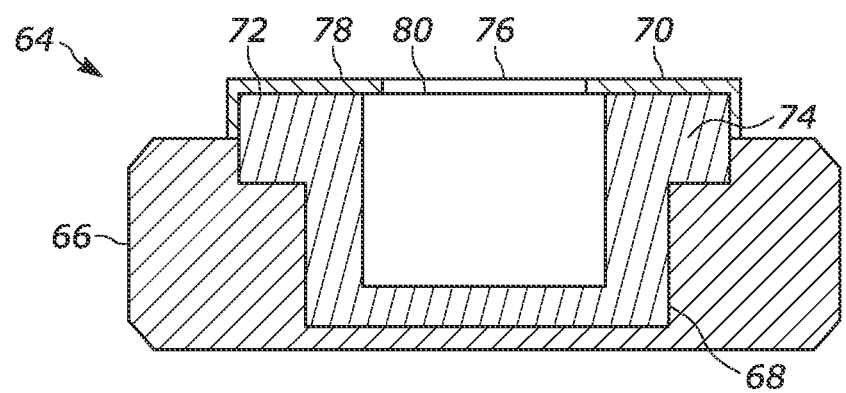
FIG. 8 is cross-sectional view of a vaginal dilator assembly according to an exemplary aspect of the present disclosure.
Figure 9:
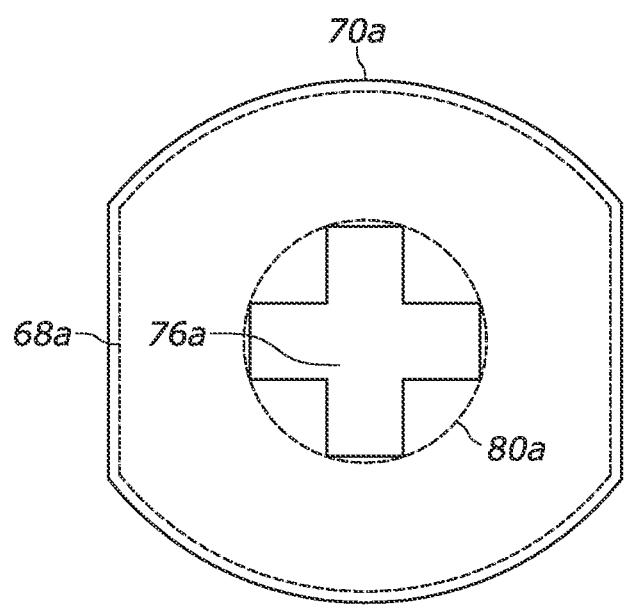
FIG. 9 is a top view of an end cap over a top portion of an adapter of a vaginal dilator assembly according to am exemplary aspect of the disclosure.

Referring to FIGS. 8 and 9, a vaginal dilator assembly 64 can comprise a base 66 and adapter 68 and can further comprise a cap 70 configured to fit over the top portion 72 of the adapter body 74 of adapter 68. Cap 70 can define an opening 76 through a top portion 78 thereof that is smaller than the adapter body opening 80. Cap opening 76 is configured to longitudinally stabilize a vaginal dilator smaller than adapter body opening 80. FIG. 9 illustrates a cross shaped opening 76*a* but the cap opening can have any suitable configuration so long as the cap can stabilize a vaginal dilator. For example, the opening can be a single slit, circular, triangular, etc. to allow the bottom of the dilator to pass through it. The cap be fabricated from an elastomer, such as silicone, or other suitable material.

Figure 10:
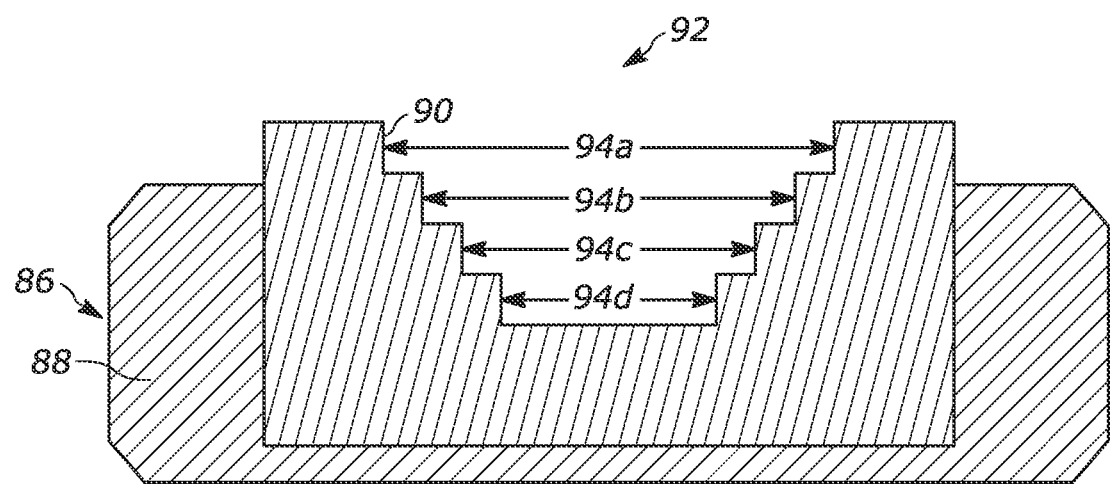
FIG. 10 is a cross-sectional side view of a base of a vaginal dilator kit according to an exemplary aspect of the present disclosure.

Referring to FIG. 10, in certain aspects a vaginal dilator kit is provided that includes a base 86 comprising a base body 88 having an inner wall 90 defining a recess 92 aligned with the longitudinal axis of base 86. Recess 92 has a plurality of step tapered sections 94. For example, the first tapered section 94*a* can have a width of approximately 1½ inches; the second tapered section 94*b* can have a width of approximately 1⅜ inches; the third tapered section 94*c* can have a width of approximately 1¼ inches; and the fourth tapered section 94*d* can have a width of approximately 1⅛ inches. Such widths are only exemplary and the tapered sections of the recess can have other widths depending on the diameter of the vaginal dilator that is to be used. Further, the number of tapered sections can be more or less than four. The kit can also include a plurality of vaginal dilators (not shown) having different diameters. Each of the plurality of vaginal dilators can be configured to be axially aligned and securely fitted into one of the step tapered sections 94 of recess 92 of base 86. Thus, instead of having various sized adaptors to fit into the base, the base itself can have a recess with tapered sections to fit different dilator diameters.

Each of the disclosed aspects and embodiments of the present disclosure may be considered individually or in combination with other aspects and embodiments as well as with respect to other vaginal dilators. Further, while certain features of embodiments may be shown in only certain figures, such features can be incorporated into or deleted from other embodiments shown in other figures or otherwise disclosed in the specification. Additionally, when describing a range, all points within that range are included in this disclosure.

The invention claimed is:

1. A vaginal dilator assembly comprising:
   a base comprising a base body having an inner portion and defining a recess aligned with the longitudinal axis of the base; and
   an adapter comprising an adapter body comprising a head defining an opening configured to receive a vaginal dilator through a top portion thereof and a shank depending from the head, the adapter body axially aligned with the recess of the base body, at least the shank having an outer portion complimentary to the inner portion of the base body such that the adapter body is non-rotatably fitted into the recess of the base body.

2. The vaginal dilator assembly of claim 1, further comprising a vaginal dilator axially aligned with and received by the opening of the head.

3. The vaginal dilator assembly of claim 1, wherein a width of the head is greater than a width of the shank.

4. The vaginal dilator assembly of claim 1, wherein the opening is configured to receive vaginal dilators having different sized diameters.

5. The vaginal dilator assembly of claim 1, wherein:
   the recess of the base body is a stepped recess defined by the inner portion of the base body; and
   the outer portion of the shank that is complimentary to the inner portion of the base is at least an outer surface of the shank.

6. The vaginal dilator assembly of claim 1, wherein inner portion of the base body defines a channel that extends at least partially along the longitudinal axis of the base and the outer portion of the adapter body comprises a notch or other projection that is complimentary to the channel of the base body.

7. The vaginal dilator assembly of claim 1, wherein the base comprises a plurality of securers circumferentially disposed about the base body and configured to receive and secure elastic stays or sutures to the base.

8. The vaginal dilator assembly of claim 7, wherein the plurality of securers comprises orifices, channels, boat-style cleats, wedge-shaped flaps, grooves, or posts.

9. The vaginal dilator assembly of claim 7, wherein the plurality of securers comprises four or more securers equidistantly spaced from each other.

10. The vaginal dilator assembly of claim 1, further comprising a cap configured to fit over the top portion of the head, the cap defining an opening through a top portion thereof that is smaller than the opening of the head, the cap opening configured to longitudinally stabilize a vaginal dilator smaller than the adapter body opening of the head.

11. A vaginal dilator device comprising:
    a base comprising a base body having an inner wall defining a recess aligned with the longitudinal axis of the base, the recess having a plurality of step tapered sections sized and configured to receive vaginal dilators having different diameters.

12. A vaginal dilator kit comprising the vaginal dilator device of claim 11 and further comprising a plurality of vaginal dilators having different diameters, each of the plurality of vaginal dilators configured to be axially aligned and securely fitted into one of the step tapered sections of the recess of the base.

* * * * *